United States Patent [19]

Miyata et al.

[11] Patent Number: 4,912,319

[45] Date of Patent: Mar. 27, 1990

[54] DETECTOR DEVICE FOR MIXING RATIO FOR GASOLINE AND ALCOHOL OR THE LIKE

[75] Inventors: Shigeru Miyata; Yoshihiro Matsubara; Kiyotaka Ohno, all of Nagoya, Japan

[73] Assignee: NGK Spark Plug Co., Ltd., Nagoya, Japan

[21] Appl. No.: 160,632

[22] Filed: Feb. 26, 1988

[30] Foreign Application Priority Data

Feb. 26, 1987 [JP] Japan .................... 62-43960

[51] Int. Cl.[4] .................. H01J 5/16; G01N 21/41
[52] U.S. Cl. .................. 250/227.14; 250/577; 356/136
[58] Field of Search .................. 356/133, 135, 136; 250/227, 205, 238, 577

[56] References Cited

U.S. PATENT DOCUMENTS

| | | | |
|---|---|---|---|
| 3,639,770 | 2/1972 | Zizelmann | 356/136 |
| 4,306,805 | 12/1981 | Arrington | 356/136 |
| 4,320,291 | 3/1982 | Uramoto | 356/136 |
| 4,451,147 | 5/1984 | Dobes et al. | 356/135 |
| 4,699,511 | 10/1987 | Seaver | 356/136 |
| 4,704,029 | 11/1987 | Van Heuvelen | 356/136 |
| 4,749,274 | 6/1988 | Aoki et al. | 356/136 |

FOREIGN PATENT DOCUMENTS

0011637 1/1986 Japan .................... 356/136

*Primary Examiner*—David C. Nelms
*Assistant Examiner*—Michael Messinger
*Attorney, Agent, or Firm*—Cooper & Dunham

[57] ABSTRACT

A detector device for mixing ratio for gasoline and alcohol include an optically permeable column, one end of which is coated with a light-reflective layer. The circumferential surface of the column is at least partly immersed in mixing liquid of gasoline and alcohol.

The light beams enter the column to be incident on said circumferential surface of the column and reflect from the circumferential surface to be incident on said light reflective-layer to reflect therefrom. The reflected light beams impinge on a photo diode which outputs in accordance with the intensity of the light beams impinged.

The diametrical and lengthwise dimension of the column being determined such as to provide incidence angles of the reflected light beams changing from a minimum angle corresponding to the critical angle when the mixing liquid ratio is at the lower limit of the predetermined range to a maximum angle corresponding to the critical angle when the mixing liquid ratio is at the upper limit of the predetermined range.

11 Claims, 8 Drawing Sheets

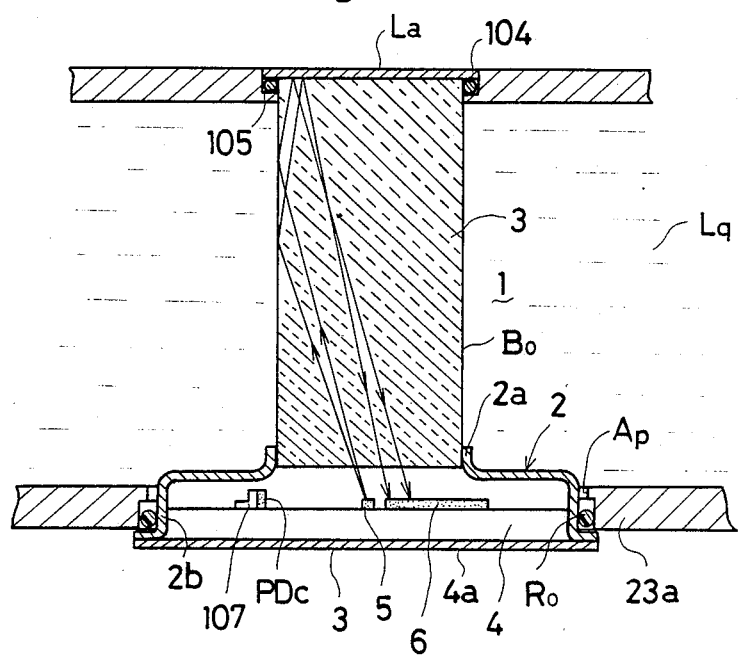

DETECTOR DEVICE FOR MIXING RATIO FOR GASOLINE AND ALCOHOL OR THE LIKE

BACKGROUND OF THE INVENTION

1. Field of the Invention

This invention relates to a detector device in which a mixing ratio of such as, for example, gasoline and alcohol is optically measured, and particularly concerned to the detector device suited for use in fuel of internal combustion engine.

2. Description of the Prior Art

In an internal combustion engine for motor vehicle, it has been suggested that mixing liquid of gasoline and alcohol would be applied to as a combustible fuel. When the liquid fuel is applied to as this combustible fuel it is necessary to continuously detect mixing liquid ratio of alcohol and gasoline so that an automatic combustion control unit may work to insure the most appropriate quantity of fuel injection in order to obtain an optimum output of the engine.

For this purpose, a detector device is provided which includes an optically permeable column. A circumferential surface of the column is immersed in mixing liquid of gasoline and alcohol.

Light beams of a light source enter from one end of the column to be incident on the circumferential surface of the column at an angle more than critical angle, and totally reflect at the circumferential surface. The totally reflected light beams emerge from the other end of the column to impinge on a photo diode which produces an output in accordance with an intensity of the light beams impinged on.

The theory is such that the critical angle changes depending upon the mixing degree of the mixing liquid, measuring the output form the photo diode enables to obtain the mixing liquid ratio.

In this device, however, the light source and the photo diode are axially located at both sides of the column, thus requiring two cases to discretely enclose the light source and the diode to add the number of assembly process.

In addition, axially dimension of the prior device inevitably become greater to render difficult to make a whole structure compact.

Therefore, it is an object of this invention to provide the detector device which is capable of making the optically permeable column compact, and contributing to cost-saving and reduction of assembly processes.

It is another object of this invention to provide the detector device which is capable of directing only required quantity of light beams to the photo diode, thus enabling to measure the mixing ratio of the mixing liquid with high accuracy.

According to this invention, there is provided a detector device comprising; the optically permeable column, one end which is coated with a light-reflective layer, at least the circumferential surface of said column being partially immersed in the mixing liquid of, such as, gasoline and alcohol or the like; a light emitting diode and photo diode each placed at opposite side to the light-reflective layer to align along a diametrical direction of the column; light beams from the light emitting diode forming such a light path that the light beams pass the column to be incident on the circumferential surface of said column and reflect form the circumferential surface to be incident on the light reflective-layer to reflect therefrom to impinge on the photo diode, the light beams incident on the circumferential surface of the column at less than the critical angle being refracted to said mixing liquid while the light beams incident on the circumferential surface at more than the critical angle being totally reflected, the critical angle depending on a mixing degree of the mixing liquid; and a diametrical and lengthwise dimension of the column being determined such as to provide incidence angles of the reflected light beams changing from a minimum angle corresponding to the critical angle when the mixing liquid ratio is at the lower limit of the predetermined range to a maximum angle corresponding to the critical angle when the mixing liquid ratio is at the upper limit of the predetermined range.

BRIEF DESCRIPTION OF THE DRAWINGS

FIG. 14 is a view corresponding to FIG. 1 according to other modified form, but making no part of the invention.

DETAILED DESCRIPTION OF THE INVENTION

Figure 1:
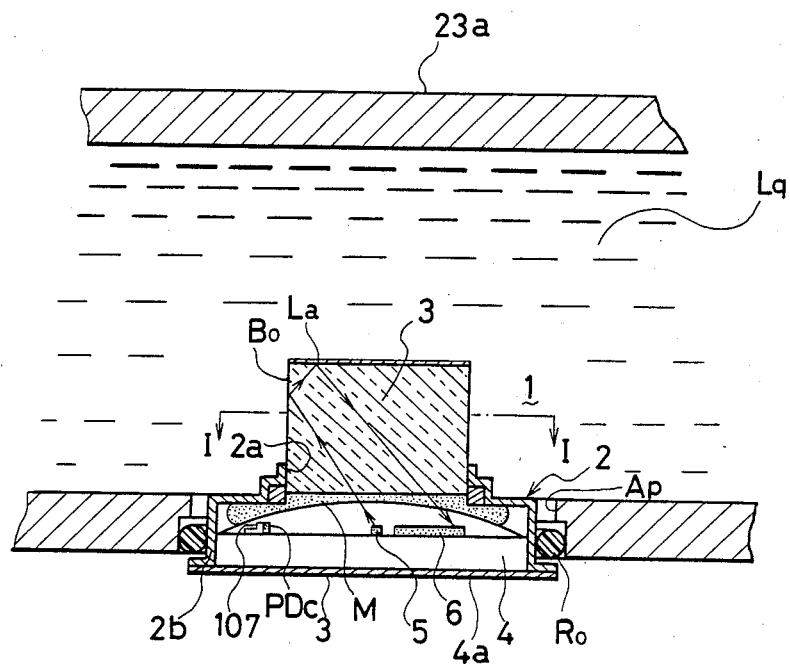
FIG. 1 is a longitudinal cross sectional view of a detector device.
Figure 2:
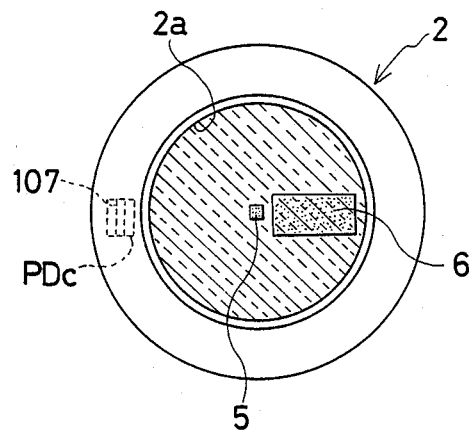
FIG. 2 is a latitudinal cross sectional view along line I—I.

Referring first to FIGS. 1 and 2 of the drawings, numeral 1 designates a detector device according to the invention. The detector device 1 is placed at an intermediate pipe 23a connected between a fuel reservoir 20 mixing liquid flow of gasoline and alcohol (Lq) as described hereinafter in FIG. 7. The pipe 23a has an aperture (Ap) at its outer wall to communicate an inside space with the atmosphere.

To an inner rim of the aperture (Ap), is a flatten case 2 liquid-tightly secured by means of an O-ring (Ro). An upper open end of the case 2 is reduced to have a diameter-reduced ring portion 2a into which a lower end of a column 3 is liquid-tightly telescoped. The column 3 is made of a flint glass to have an optically permeable property, upper end of which is coated with a light-reflective layer (La) by means of an electrical deposition, for example.

Into the case 2, is a pedestal 4 enclosed on which a light emitting diode 5 and a photo diode 6 are placed along a diametrical direction of the column 3.

In alignment with both the diodes 5 and 6 is a compensation photo diode (PDc) mounted on the pedestal 4 by means of support 107 remote from the photo diode 6. These three diodes 5, 6 and PDc are moulded by a transparent epoxy to form an arched surface. Between this arched surface and the lower end of the column 3, is a transparent mould layer (M) provided to remove gaseous components presented therebetween. A base plate 4a is secured to the lower open end 2b of the case 2 by means of welding or the like.

In this situation, light beams from the diode 5 enters the column 3 from its lower end to be incident on a circumferential surface (Bo) which is in direct contact with the mixing liquid (Lq). The light beams incident on the circumferential surface (Bo) at less than a critical angle, are refracted to the mixing liquid (Lq), while the light beams incident on the surface (Bo) at more than the critical angle, being totally reflected with the critical angle depending upon the mixing liquid ratio. The reflected light beams from the surface (Bo), is incident on the layer (La), and reflects therefrom to emerge from the lower end of the column 3 so as to impinge on the photo diode 6 which produces an output in accordance with the intensity of light beams impinged thereon.

Among the light paths formed as above, particular light paths are allowed to determine the most appropriate diametrical and lengthwise dimension of the column 3.

That is, such light paths are allowed as to provide incident angles of the reflected light beams continuously changing from a minimum corresponding to the critical angle when the mixing liquid ratio is at the lower limit of the predetermined range to a maximum corresponding to the critical angle when the mixing liquid ratio is at the upper limit of the predetermined range.

However, since the diode 5 is eccentrically located, there is possibility that the light beams firstly incident on the light-reflective layer (La), may be incident on the surface (Bo) to totally reflect therefrom so as to impinge on the photo diode 6.

For this possibility, a light paths is particularly depicted at arrow (Pt).

Figure 3:
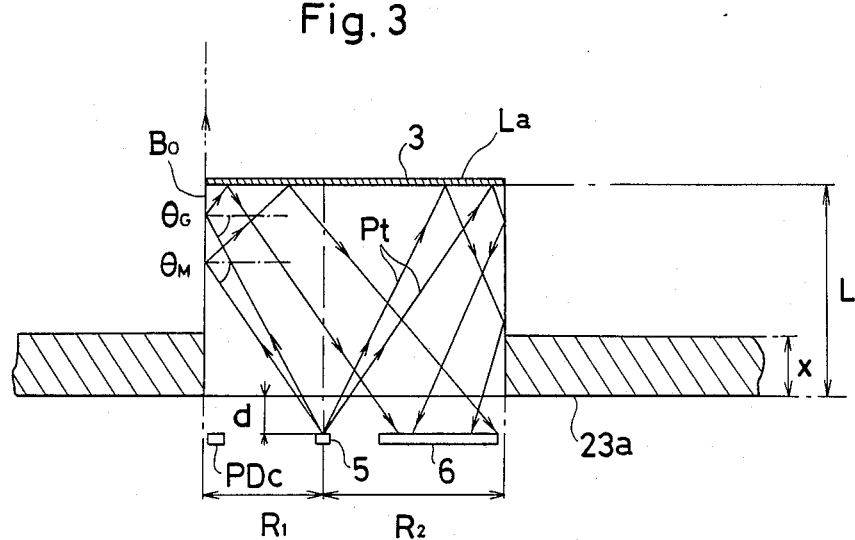
FIGS. 3, 4, 5, and 6 are schematic views shown for the purpose of elucidating a principle of the invention.
Figure 4:
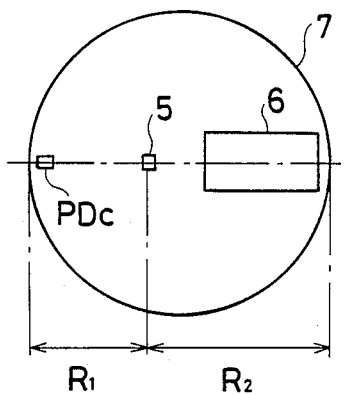

Now, FIGS. 3 and 4 are schematic views shown to supply geometrical relationship between the light paths and the column 3.

In these Figures, the mixing liquid ratio of gasoline and alcohol is supposed to continuously vary from 100% to 0% with taking an extreme case into consideration. It, however, stands as a matter of course that the mixing liquid ratio may be within the predetermined range varying from 30% to 60% based on the actuality.

As seen in FIG. 3, denotation ($\theta M$) shows a minimum corresponding to the critical angle when gasoline component is at the lower limit (0%). At this time, the light beams reflected from the surface (Bo) escape as shown at phantom lines in FIG. 3.

On the other hand, denotation ($\theta G$) shows a maximum corresponding to the critical angle when gasoline component is at the upper limit (100%). At this time, the light beams reflected from the surface (Bo) escape as shown at above-identified phantom lines in FIG. 3.

Denotation $R_1$ shows a distance measured from the diode 5 to the outer periphery of the column 3. Denotation $R_2$ shows a distance obtained by subtracting the distance $R_1$ from the outer diameter of the column 3. Denotation (d) is an axial dimension expressing how far the diode 5 is distanced from the lower end of the column 3.

Denotations L and x, in turn designates a lengthwise dimension of the column 3, and a thickness dimension of the pipe 23a.

With these denotations and the geometrical relationship, the following representations are apparently obtained.

$$R_1 \cdot \tan(\theta M) \geq (d+x); \quad L \geq R_1 \cdot \tan(\theta G) - d;$$

Since dimensions of ($\theta M$), (d+x), ($\theta G$) and (d) are known, these dimensions of $R_1$ and L are concretely determined.

In connection with the distance $R_2$, the relationship $(2L+d-x)/\tan(\theta G) \geq R_2 \geq (L+d)/\tan(\theta M)$ is obtained as elucidated hereinafter.

Figure 5:
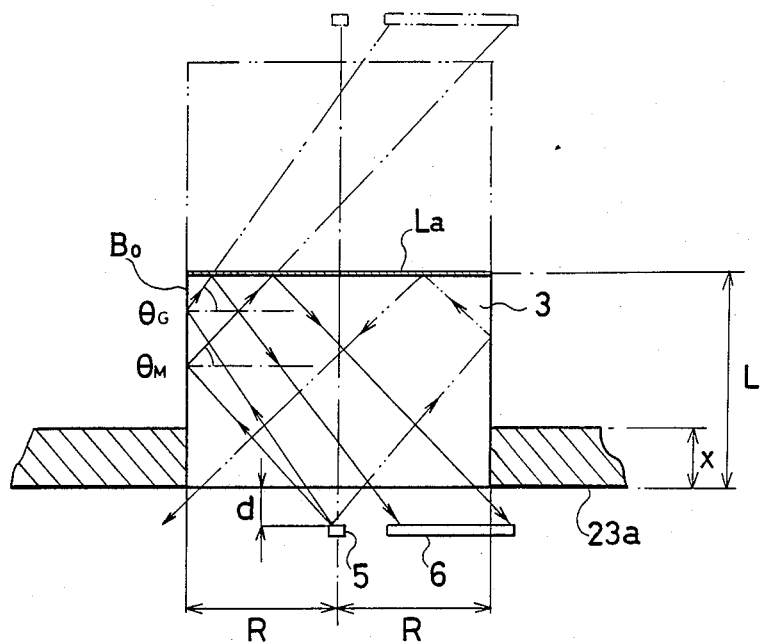
Figure 6:
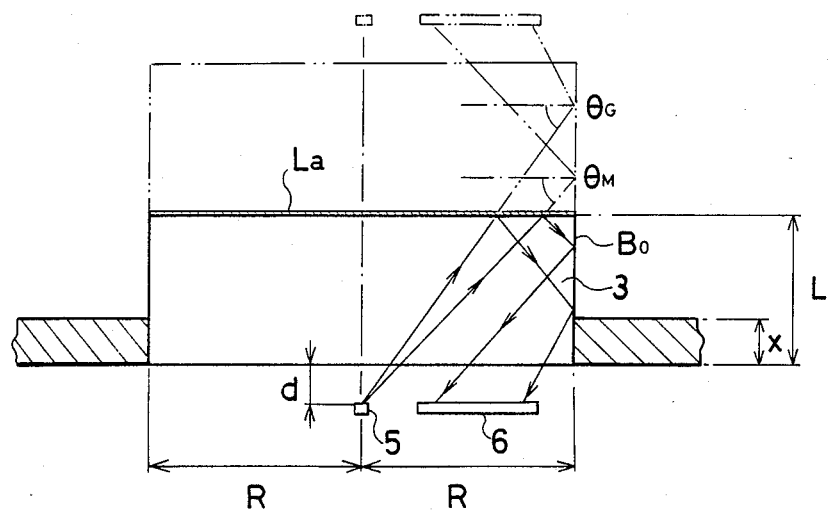

Further, FIGS. 5 and 6 show other examples in which the light emitting diode 5 is aligned with a central axis of the column 3. In this situation, representations $R \cdot \tan(\theta M) \geq (x+d)$ and $(L+d) \geq R \cdot \tan(\theta G)$ are obtained. From the two representations, expressions $R \geq (x+d)/\tan(\theta M)$; and $L \geq R \cdot \tan(\theta G) - d$; are derived. Where, denotations R represents a radius of the column 3.

Particularly in the case of FIG. 6, the light beams of the diode 5 firstly incident on the light-reflective layer (La), is incident on the surface (Bo) to totally reflect therefrom so as to impinge on the photo diode 6.

In this example, relationships among the dimensions of R, L, d, x, ($\theta M$) and ($\theta G$), are derived as follows:

$$(2L+d-x) \geq R \cdot \tan(\theta G); \quad R \cdot \tan(\theta M) \geq (L+d);$$

From these relationships, $$(2L+d-x)/\tan(\theta G) \geq R \geq (L+d)/\tan(\theta M).$$

Figure 7:
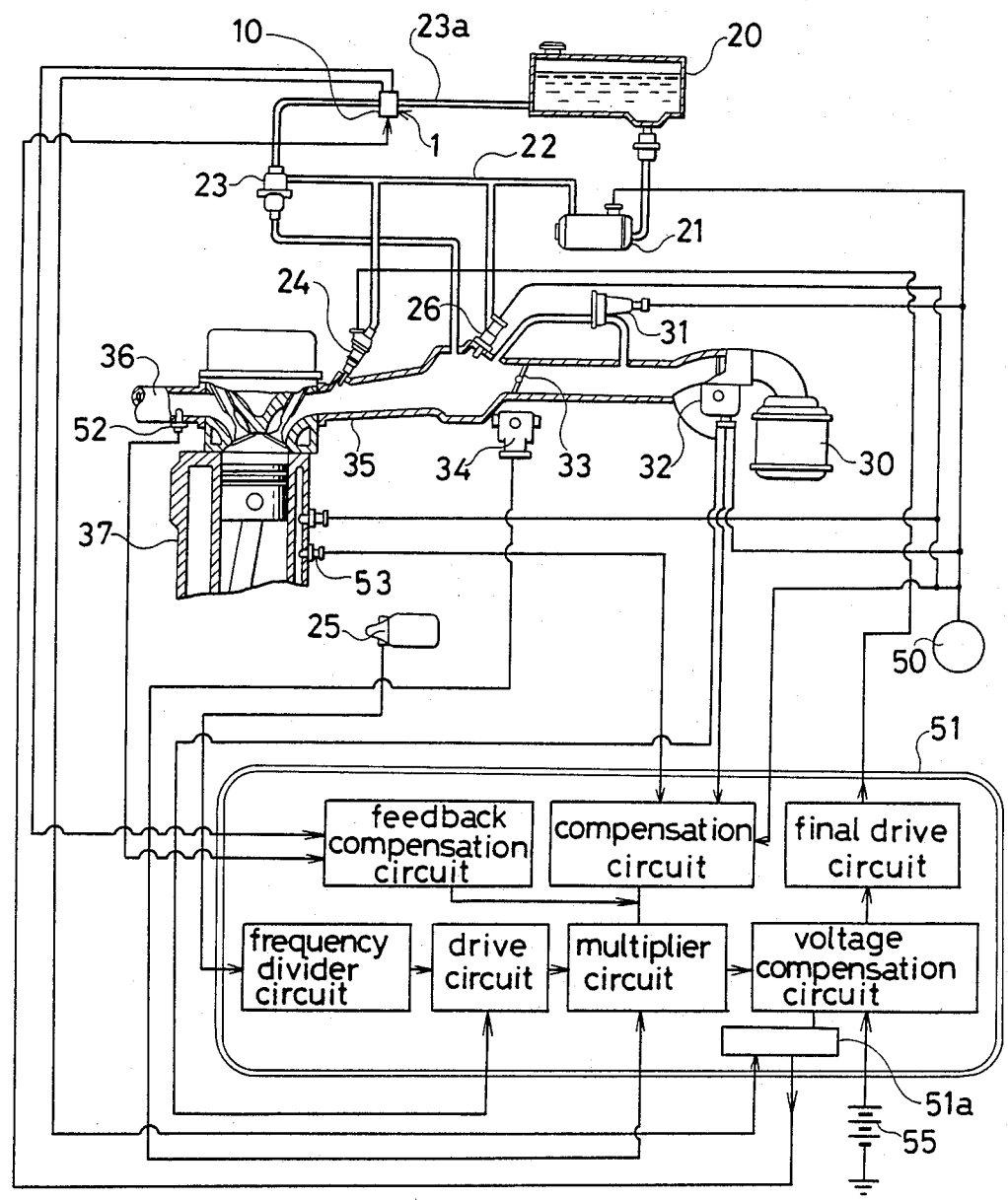
FIG. 7 is a systematic view of an internal combustion engine for use in motor vehicle.

Now, FIG. 7 shows a control system in which the detector device 1 is incorporated into internal combustion engine for motor vehicle. In FIG. 7 numeral 37 designates an engine cylinder, numeral 50 being an ignition key, numeral 51 being a control circuit, numeral 55 being a battery cell acting as a power source, numeral 20 being the fuel reservoir. Numeral 21 designates a fuel pump, numeral 23 being a pressure regulator which is introduced from the fuel reservoir 20 by way of the intermediate pipe 23a on which the detector device 1 is mounted.

Numeral 24 shows a fuel injector, numeral 25 being an ignition coil, numeral 26 being a cold start injector, numeral 30 being an air cleaner, numeral 31 being an air valve, numeral 32 being a air flow meter, numeral 33 being a throttle valve, numeral 34 being a position sensor for the throttle valve 33, numeral 35 being an intake pipe, numeral 36 being a exhaust pipe, numeral 52 being a sensor for detecting air-fuel ratio of the mixing liquid (Lq), numeral 53 being a temperature sensor for cooling water which is circulating in a jacket of an engine cylinder 37.

In operation, actuating an engine key 50 permits the engine to run, while supplying the power source to the control circuit 51. In accordance with the activated control circuit 51, the mixing liquid (Lq) of gasoline and alcohol in the reservoir 20 is introduced into the injector 24 through a fuel pipe 22 by means of the pump 21. At this time, the injector 24 works to feed the mixing liquid (Lq) into the intake pipe 35 as liquid fuel at the most appropriate quantity of injection electronically calculated to the working condition of the engine.

Meanwhile, the control circuit 51 allows to apply a voltage across the light emitting diode 5, so that the diode 5 emits the light beams to follow the light paths as described in FIGS. 3 and 4. The photo diode 6 on which the reflected light beams impinged, produces an output which is fed to the control circuit 51 through an input arrangement 51a.

In this instance, variation of the mixing liquid ratio changes its refraction index to cause alteration of the critical angle when the light beams are incident on the surface (Bo). The change of the critical angle influences on the quantity of the light beams impinged on the diode 6 to change the output therefrom. From the change of the refraction index of the mixing liquid (Lq), the relationship between the mixing liquid ratio and the output form the photo diode 6, has previously been able to obtained as accumulated data. The data enables the control circuit 51 to calculate the most appropriate quantity of injection to maintain a favorable output of the engine.

Figure 8:
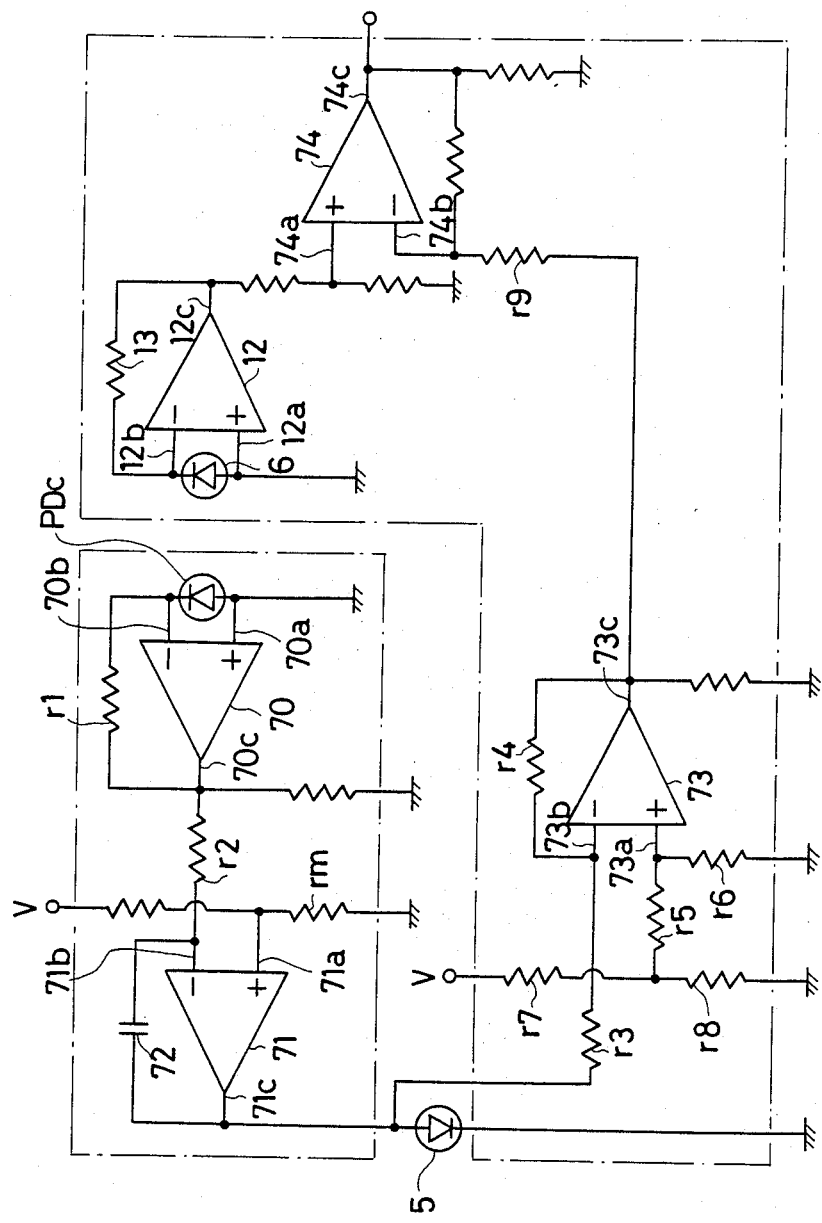
FIG. 8 is a wiring diagram of an electrical circuit.

Now, an electrical circuit for temperature compensation is shown in FIG. 8 in which the photo diode 6 is connected across positive and negative terminals 12a and 12b of an amplifier 12, while the negative terminal 12b being connected to an output terminal 12c of the amplifier 12 through an electrical resistance 13.

The temperature compensation photo diode (PDc) is in the form of rectangular chip, and located such that the diode (PDc) is exposed to a constant quantity of the reflected light irrespective of the variation of the mixing liquid ratio.

The diode (PDc) is incorporated into an electrical circuit as shown in FIG. 8. The diode (PDc) is connected across positive and negative terminals 70a, 70b of first amplifier 70. A common point of the negative terminal 70b and the diode (PDc) is connected to an output terminal 70c of the amplifier 70 by way of an electrical resistance r1. The output terminal 70c is connected to a negative terminal 71b of second amplifier 71 through an electrical resistance r2. The amplifier 71 has a positive terminal 71a grounded through a suitable resistance (rm). Across the negative terminal 71b and an output terminal 71c, is a condenser 72 connected to prevent an adverse hunting action. A common point of the condenser 72 and the output terminal 71c is grounded by way of the light emitting diode 5. A common point of the output terminal 71c and the light emitting diode 5 is connected to a negative terminal 73b of third amplifier 73 through an electrical resistance r3. The amplifier 73 is adapted to connect the negative terminal 73b to an output terminal 73c through an electrical resistance r4. To a positive terminal 73a, is the predetermined input voltage (V) supplied through a resistance r5. The predetermined input voltage is equivalent to the voltage proportionally divided by electrical resistances r7 and r8. The ratio of the resistances r3 and r4 is determined to correspond to that of the resistances r5 and r6. A common point of the resistance r4 and the positive terminal 73c is connected to a negative terminal 74b of fourth amplifier 74 by way of a resistance r9. The amplifier 74 serves as an calculator into which, by way of its positive terminal 74a, an output of an amplifier 12 is fed to which the photo diode 6 is connected.

Simultaneously, an output of the third amplifier 73 is fed into the calculator by way of the negative terminal 74b. The fourth amplifier 74 produces an output through its output terminal 74c in accordance with the output difference between the amplifiers 12 and 73.

When the positive terminal 71a is under a constant voltage, the amplifier is activated to control the quantity of current supplied to the diode 5 to hole the diode (PDc) at a predetermined output level, and leading to a uniform output of the photo diode 6 in the case in which the refraction index of the mixing liquid of gasoline and alcohol remains unchanged.

Figure 9:
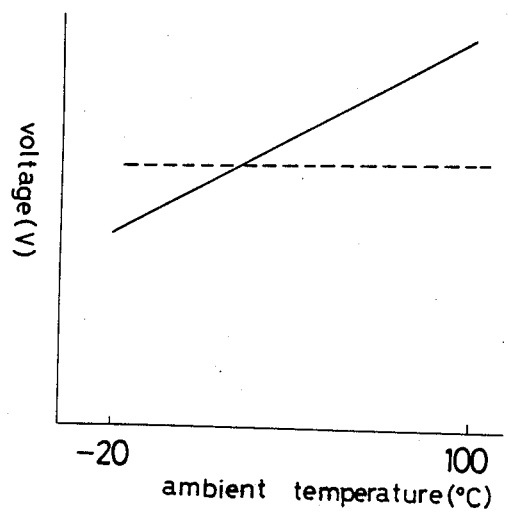
FIG. 9 is a graph showing a relationship between an output (V) of a photodiode and the ambient temperature (T)

The refraction index of the mixing liquid however, changes in accordance with the ambient temperature in a manner that the relationship between an ambient temperature (T) and the output (V) of the photo diode 6, is as seen at solid line in FIG. 9.

Figure 10:
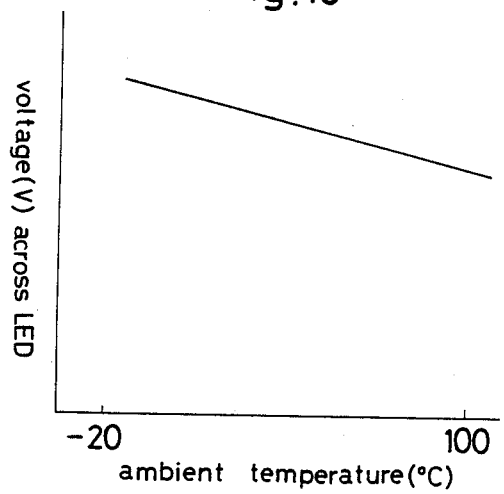
FIG. 10 is a graph showing a relationship between an output (V) of a light emitting diode and the ambient temperature (T)

The relationship between the ambient temperature (T) and the voltage drop (V) across the light emitting diode 5 is as seen at solid line in FIG. 10 in which the voltage drop (V) decreases with the increase of the ambient temperature (T).

Figure 11:
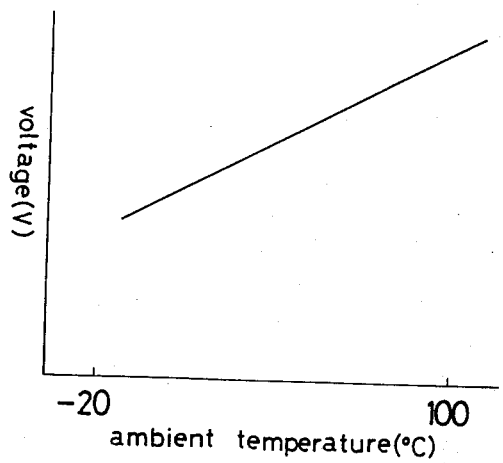
FIG. 11 is a graph showing a relationship between the ambient temperature (T) and voltage (V) applied to second amplifier.

In so doing, the voltage applied across the light emitting diode 5, is fed to the third amplifier 73 through the positive terminal 73a, so that the amplifier 73 allows the output terminal 73c to produce a voltage (V) which progressively steps up with the increase of the ambient temperature (T) as depicted in FIG. 11. The voltage, thus stepping up, is applied to the diode 5 through the output terminal 71c of the amplifier 71 to decrease the light emitting degree of the diode 5. This leads to decreasing the output of the photo diode 6, so that the certain level of the output form the photo diode 6 is maintained regardless of the ambient temperature as seen at dotted lines in FIG. 9.

Further, the light emitting diode 5 deteriorates with long periods of operation in such an extent that the light intensity reduces by a few percent with one thousand operating hours. The quantity of the light beams to which the diode (PDc) is exposed, reduces to drop the output, eventually decreasing the output of the amplifier 70. The decreased output of the first amplifier 70 is applied to the negative terminal 71b of the second amplifier 71. The amplified output is fed through the output terminal 71c across the diode 5 to compensate for the loss of the light emitting quantity.

With long period of use, the deposit appears on the outer surface of the column 3, absorbing the light beams of the diode 5 so as to reduce the output of the photo diode 6. The light beams lost by the absorption is compensated in the same manner as the above case in which the light emitting diode 5 has deteriorated.

Figure 12:
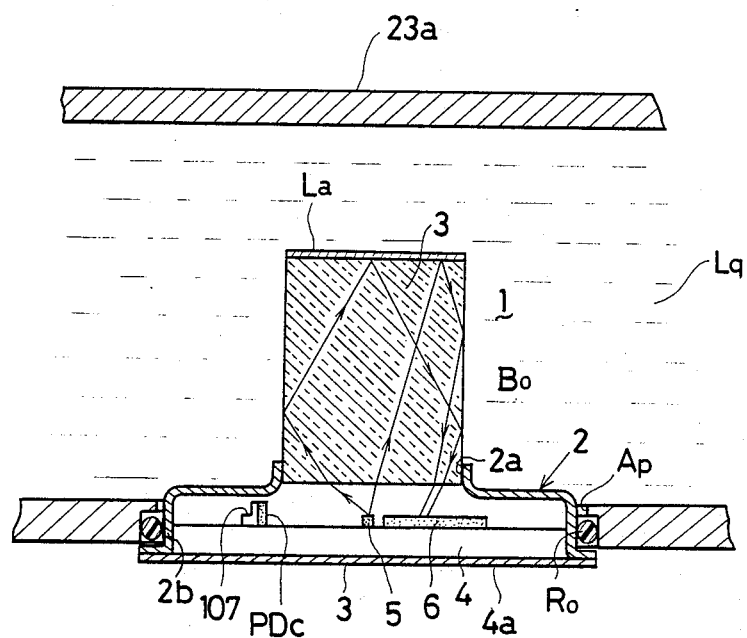
FIG. 12 is a view corresponding to FIG. 1 according to a modified form, but making no part of the invention.
Figure 13:
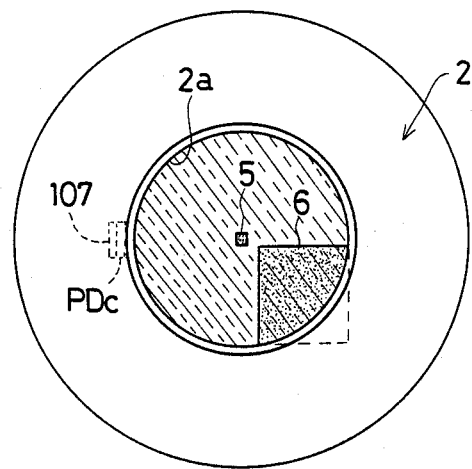
FIG. 13 is a view corresponding to FIG. 2 according to the modified form, but making no part of the invention.

Now, FIGS. 12 and 13 show example in which the light reflective-layer (La) is employed, but the principle mentioned in FIGS. 3, 4, 5 and 6 is not applied to diametrical and lengthwise relationship of the column 3 of FIGS. 12 and 13.

In FIGS. 12 and 13, the same reference numerals designate the same parts of FIGS. 1 and 2 for the sake of convenience, but example of FIGS. 12 and 13 makes no substantial part of this invention.

In FIG. 14, upper end of the column 3 extends across the mixing liquid flow to be received by a hole 104 provided with a wall of the pipe 23a under the same condition of FIGS. 12 and 13. An O-ring 105 liquid-tightly seals a clearance in the hole 104.

It is appreciated that the light-reflective layer may be made form a metallic foil, mirrored plastic foil or sputtering instead of the electrical deposition. Further, a reinforced glass or corrosion-resistant plastic material may be used instead of the flint glass.

It is noted that instead of the mixing liquid of gasoline and alcohol, sucrose or saline water may be employed to continuously detect concentration of the solution.

What is claimed is:

1. A detector device for detecting the mixing ratio of gasoline and alcohol or the like comprising:
    an optionally permeable column, one end of which is coated with a light-reflective layer, at least a circumferential surface of said column being partially immersed in the mixing liquid of gasoline and alcohol;
    a light emitting diode and a photo diode each placed at an opposite side to said light-reflective layer aligned along a diametrical direction of said column;
    light beams from said light emitting diode forming such a light path that said light beams pass within said column to be incident on said circumferential surface of said column and reflect from said circumferential surface of said column to be incident on said light-reflective layer to reflect therefrom to impinge on said photo diode, the light beams incident on said circumferential surface of said column at less than a critical angle being refracted to said mixing liquid while the light beams incident on said circumferential surface at more than the critical angle being totally reflected, the critical angle depending on a mixing degree of said mixing liquid; and
    the diametrical and lengthwise dimension of said column being determined such as to provide incidence angles of said reflected light beams changing from a minimum angle corresponding to the critical angle when said mixing liquid ratio is at the lower limit of the predetermined range to a maximum angle corresponding to the critical angle when said mixing liquid ratio is at the upper limit of the predetermined range.

2. A detector device for detecting the mixing ratio of gasoline and alcohol or the like as recited in claim 1 in which said light emitting diode is located to align with the central axis of said column.

3. A detector device for detecting the mixing ratio gasoline and alcohol or the like as recited in claim 2 in which one end of said column is interfit into an aperture of a pipe into which the mixing liquid flows, radius dimension R and lengthwise dimension L are derived as follows:

$$L \geq R \cdot \tan(\Theta G) - d; \quad R \geq (x+d)/\tan(\Theta M);$$

Where L: length of the column,
d: axial dimension expressing how far the light emitting diode is distanced from the lower end of the column,
x: thickness of the pipe,
$\Theta M$: minimum corresponding to the critical angle when the mixing liquid ratio is at the lower limit of the predetermined range,
$\Theta G$: maximum corresponding to the critical angle when the mixing liquid ratio is at the upper limit of the predetermined range.

4. A detector device for detecting the mixing ratio of gasoline and alcohol or the like as recited in claim 1 in which said optically permeable column is made of flint glass.

5. A detector device for detecting the mixing ratio of gasoline and alcohol or the like as recited in claim 4 in which said optically permeable column is made of flint glass.

6. A detector device for detecting the mixing ratio of gasoline and alcohol or the like as recited in claim 1 in which a temperature compensation photo diode is provided with an electrical circuit, so that a constant output is generated from said temperature compensation photo diode by controlling current supply toward said light emitting diode.

7. The detector device for detecting the mixing ratio of gasoline and alcohol or the like as recited in claim 1 in which one end of said column is interfit into an aperture of a pipe into which the mixing liquid flows, diametrical dimension ($R_1 + R_2$) and lengthwise dimension L are derived as follows:

$$L \geq R_1 \cdot \tan(\Theta G) - d; \quad R_1 \cdot \tan(\Theta M) \geq (d+x);$$

$$(2L + d - x)/\tan(\Theta G) \geq R_2 \geq (L+d)/\tan(\Theta M)$$

Where: L: length of the column,
d: axial dimension expressing how far the light emitting diode is distanced from the lower end of the column,
x: thickness of the pipe,
$R_1$: distance measured from the light emitting diode to the periphery of the column,
$R_2$: distance obtained by substracting the distance $R_1$ from the diameter of the column,
$\Theta M$: minimum corresponding to the critical angle when the mixing liquid ratio is at the lower limit of the predetermined range,
$\Theta G$: maximum corresponding to the critical angle when the mixing liquid ratio is at the upper limit of the predetermined range.

8. A detector device for detecting the mixing ratio of gasoline and alcohol or the like comprising:
    an optically permeable column, one end of which is coated with a light-reflective layer, at least a circumferential surface of said column being partially immersed in the mixing liquid of gasoline and alcohol;
    a light emitting diode and a photo diode each placed at an opposite side to said light-reflective layer to align along a diametrical direction of said column;
    light beams from said light emitting diode forming such a light path that said light beams pass within said column to be incident on said light reflective layer, and reflects therefrom to be incident on said circumferential surface of said column and reflects there from to impinge on said photo diode, the light beams incident on said circumferential surface of said column at less than a critical angle being refracted to said mixing liquid while the light beams incident on said circumferential surface at more than the critical angle being totally reflected, the critical angle depending on a mixing degree of said mixing liquid; and
    a diametrical and lengthwise dimension of said column being determined such as to provide incidence angles of said reflected light beams changing from a minimum angle corresponding to the critical angle when said mixing liquid ratio is at the lower limit of the predetermined range to a maximum angle corresponding to the critical angle when said mixing liquid ratio is at the upper limit of the predetermined range.

9. A detector device for detecting the mixing ratio of gasoline and alcohol or the like as recited in claim 8 in which said light emitting diode is located to align with a central axis of said column.

10. A detector device for detecting the mixing ratio of gasoline and alcohol or the like as recited in claim 9 in which one end of said column is interfit into an aperture of a pipe into which the mixing liquid flows, radius dimension R and lengthwise dimension L are derived as follows:

$$(2L+d-x)\tan(\Theta G) \geqq R \geqq (L+d)/\tan(\Theta M);$$

Where L: length of the column, d: axial dimension expressing how far the light emitting diode is distanced from the lower end of the column, x: thickness of the pipe, $\Theta M$: minimum corresponding to the critical angle when the mixing liquid ratio is at the lower limit of the predetermined range, $\Theta G$: maximum corresponding to the critical angle when the mixing liquid ratio is at the upper limit of the predetermined range.

11. A detector device for detecting the mixing ratio gasoline and alcohol or the like as recited in claim 8 in which a temperature compensation photo diode is provided with an electrical circuit, so that a constant output is generated from said temperature compensation photo diode by controlling current suppy toward said light emitting diode.

* * * * *